United States Patent
Petersen

(10) Patent No.: US 6,806,376 B2
(45) Date of Patent: Oct. 19, 2004

(54) METHOD FOR THE PREPARATION OF CITALOPRAM

(75) Inventor: Hans Petersen, Vanløse (DK)

(73) Assignee: H. Lundbeck A.S, Valby-Copenhagen (DK)

( * ) Notice: Subject to any disclaimer, the term of this patent is extended or adjusted under 35 U.S.C. 154(b) by 0 days.

(21) Appl. No.: 10/238,907

(22) Filed: Sep. 6, 2002

(65) Prior Publication Data

US 2003/0050484 A1 Mar. 13, 2003

Related U.S. Application Data

(63) Continuation of application No. PCT/DK01/00162, filed on Mar. 9, 2001.

(30) Foreign Application Priority Data

Mar. 14, 2000 (DK) .................... 2000 00415

(51) Int. Cl.⁷ ............................. C07D 307/78

(52) U.S. Cl. ...................... 549/467; 549/469

(58) Field of Search ................. 549/467, 469

(56) References Cited

U.S. PATENT DOCUMENTS

| | | | |
|---|---|---|---|
| 3,467,675 A | 9/1969 | Petersen et al. | 260/346.2 |
| 4,136,193 A | 1/1979 | Bogeso et al. | 424/285 |
| 4,650,884 A | 3/1987 | Bogeso | 549/467 |
| 4,943,590 A | 7/1990 | Boegesoe et al. | 514/469 |
| 5,296,507 A | 3/1994 | Tanaka et al. | 514/465 |
| 6,020,501 A | 2/2000 | Massonne et al. | 549/307 |
| 6,028,204 A | 2/2000 | Massonne et al. | 549/307 |
| 6,229,026 B1 | 5/2001 | Petersen | 549/467 |
| 6,258,842 B1 | 7/2001 | Petersen et al. | 514/469 |
| 6,291,689 B1 | 9/2001 | Petersen et al. | 549/467 |
| 6,310,222 B1 | 10/2001 | Ikemoto et al. | 549/467 |
| 6,365,747 B1 | 4/2002 | Dall'Asta et al. | 548/146 |
| 6,392,060 B2 | 5/2002 | Petersen et al. | 549/307 |
| 6,403,813 B1 | 6/2002 | Petersen et al. | 549/305 |
| 6,407,267 B1 | 6/2002 | Rock et al. | 549/467 |
| 6,420,574 B2 | 7/2002 | Petersen et al. | 549/467 |
| 6,426,422 B1 | 7/2002 | Petersen et al. | 549/467 |
| 6,433,196 B1 | 8/2002 | Ikemoto et al. | 549/469 |
| 6,441,201 B1 | 8/2002 | Weber | 549/468 |
| 2002/0004604 A1 | 1/2002 | Petersen et al. | 549/462 |
| 2002/0026062 A1 | 2/2002 | Petersen et al. | 549/467 |
| 2002/0035277 A1 | 3/2002 | Rock et al. | 549/467 |
| 2002/0040153 A1 | 4/2002 | Petersen | 549/467 |
| 2002/0061925 A1 | 5/2002 | Petersen et al. | 514/469 |
| 2002/0077353 A1 | 6/2002 | Petersen et al. | 514/469 |
| 2002/0087012 A1 | 7/2002 | Castellin et al. | 549/467 |
| 2002/0120005 A1 | 8/2002 | Villa et al. | 514/466 |
| 2002/0128497 A1 | 9/2002 | Bolzonella et al. | 549/467 |

FOREIGN PATENT DOCUMENTS

| | | | |
|---|---|---|---|
| EP | 1 095 926 | 5/2001 | C07C/33/46 |
| WO | 98/19511 | 5/1998 | |
| WO | 98/19512 | 5/1998 | |
| WO | 98/19513 | 5/1998 | |
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | C07D/307/87 |
| WO | 00/39112 | 7/2000 | C07D/307/87 |
| WO | 00/44738 | 8/2000 | C07D/307/88 |
| WO | 01/45483 | 6/2001 | |
| WO | 01/47877 | 7/2001 | |
| WO | 01/47909 | 7/2001 | C07D/307/87 |
| WO | 01/49672 | 7/2001 | C07D/307/87 |
| WO | 01/51477 | 7/2001 | C07D/307/87 |
| WO | 01/51478 | 7/2001 | C07D/307/87 |
| WO | 01/62754 | 8/2001 | C07D/307/87 |
| WO | 01/66536 | 9/2001 | C07D/307/87 |
| WO | 01/68628 | 9/2001 | C07D/307/87 |
| WO | 01/68631 | 9/2001 | C07D/307/87 |
| WO | 01/68632 | 9/2001 | C07D/307/87 |
| WO | 02/04435 | 1/2002 | C07D/307/87 |

OTHER PUBLICATIONS

U.S. patent application Ser. No. 10/183,958, filed Jun. 25, 2002.
U.S. patent application Ser. No. 10/186,337, filed Jun. 27, 2002.
U.S. patent application Ser. No. 10/191,808, filed Jul. 8, 2002.

(List continued on next page.)

Primary Examiner—Amelia A. Owens
(74) Attorney, Agent, or Firm—Darby & Darby

(57) ABSTRACT

The invention relates to a method for the preparation of citalopram comprising, in either order, subjecting a compound of formula

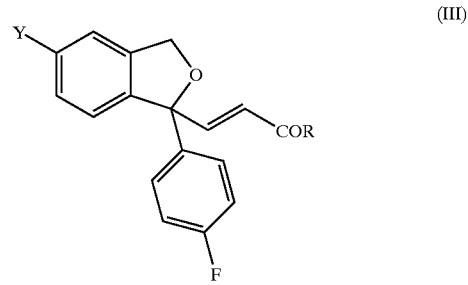

(III)

wherein Y is a cyano group or a group which may be converted to a cyano group, R is hydrogen, —O—$R^1$, $NH_2$, $NHCH_3$ or —$N(CH_3)_2$ wherein $R^1$ is selected from hydrogen, alkyl, alkenyl, alkynyl and optionally alkyl substituted aryl or aralkyl; to i) reduction of the double bond in the side chain of formula —CH=CH—COR:

ii) conversion of the group—COR or a reduced form thereof to a dimethylaminomethyl group; and iii) if Y is not cyano, conversion of the group Y to a cyano group;

followed by isolation of citalopram base or a pharmaceutically acceptable acid addition salt thereof.

10 Claims, No Drawings

OTHER PUBLICATIONS

U.S. patent application Ser. No. 10/232,944, filed Aug. 29, 2002.
U.S. patent application Ser. No. 10/233,132, filed Aug. 30, 2002.
U.S. patent application Ser. No. 10/237,145, filed Sep. 5, 2002.
U.S. patent application Ser. No. 10/228,388, filed Aug. 23, 2002.
U.S. patent application Ser. No. 10/238,843, filed Sep. 9, 2002.
U.S. patent application Ser. No. 10/242,804, filed Sep. 10, 2002.
Levy, L.F., "4–Aminophthalide and Some Derivatives", *J. Chem. Soc.* pp. 867–870 (1931).

Tirouflet, Jean, "Phtalide Substitués en 5", *Bull. Soc. Sci. de Bretagne* 26:35–43 (1951).

Forney, LeRoy S.., "Reaction of Terephthalic Acid with Formaldehyde in Sulfur Trioxide Media," *J. Org. Chem.* 35:1695–1696 (1970).

Dordor, Isabelle M. et al., "Reaction of Oxazolines with Phosphorus Oxychloride," *Tetrahedron Letters* 24:1437–1440 (1983).

Barton, Sir Derek et al., *Comprehensive Organic Chemistry. The Synthesis and Reactions of Organic Compounds*, vol. 2, pp. 1024–1025.

Bigler, Allan et al., Quantitative Structure–activity Relationships in a Series of Selective 5–HT uptake inhibitors, *Eur. J. Med. Chem.* 3:289–295 (1997).

US 6,806,376 B2

METHOD FOR THE PREPARATION OF CITALOPRAM

This application is a continuation of International Application No. PCT/DK01/00162, filed Mar. 9, 2001, the entire disclosure of which is hereby incorporated by reference, in its entirety.

The present invention relates to a method for the preparation of the well-known antidepressant drug citalopram, 1-[3-(dimethylamino)propyl]-1-(4-fluorophenyl)-1,3-dihydro-5-isobenzofuran-carbonitrile.

BACKGROUND OF THE INVENTION

Citalopram is a well-known antidepressant drug that has now been on the market for some years and has the following structure:

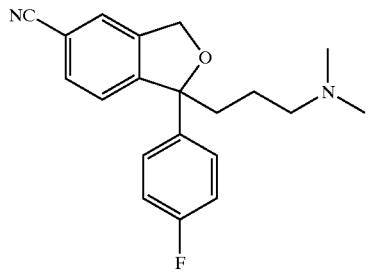

It is a selective, centrally acting serotonin (5-hydroxytryptamine; 5-HT) reuptake inhibitor, accordingly having antidepressant activities. The antidepressant activity of the compound has been reported in several publications, eg. J. Hyttel *Prog. Neuro-Psychopharmacol. & Biol. Psychiat.* 1982, 6, 277–295 and A. Gravem *Acta Psychiatr. Scand.* 1987, 75, 478–486. The compound has further been disclosed to show effects in the treatment of dementia and cerebrovascular disorders, EP-A-474580.

Citalopram was first disclosed in DE 2,657,013 corresponding to U.S. Pat. No. 4,136,193. This patent publication describes the preparation of citalopram by one method and outlines a further method, which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

International patent application No. WO 98/019511 discloses a process for the manufacture of citalopram wherein a (4-(cyano, alkyloxycarbonyl or alkylaminocarbonyl)-2-hydroxymethylphenyl-(4-fluorophenyl)methanol compound is subjected to ring closure. The resulting 5-(alkyloxycarbonyl or alkylaminocarbony)-1-(4-fluorophenyl)-1,3-dihydroisobenzofuran is converted to the corresponding 5-cyano derivative and the 5-cyano derivative is then alkylated with a (3-dimethylamino)propylhalogenide in order to obtain citalopram.

It has now, surprisingly, been found that citalopram may be manufactured by a novel favourable process where a 1-(4-fluorophenyl)-1,3-dihydroisobenzofuran is alkylated with a compound which may be converted to a dimethylaminopropyl group.

The alkylation process according to the invention is particularly advantageous because the formation of by-products by polymerisation of the alkylating agent is avoided whereby a reduction in the amount of alkylating reagent to be used is made possible. The process of the invention provides high yields.

SUMMARY OF THE INVENTION

The present invention relates to a method for the preparation of citalopram comprising subjecting, in either order, a compound of formula

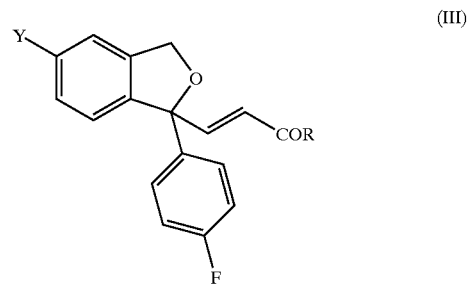

(III)

wherein Y is a cyano group or a group which may be converted to a cyano group, R is hydrogen, —O—R¹, NH₂, NHCH₃ or —N(CH₃)₂ wherein R¹ is selected from hydrogen, alkyl, alkenyl, alkynyl and optionally alkyl substituted aryl or aralkyl; to i) reduction of the double bond in the side chain of formula —CH=CH—COR; and
ii) conversion of the group —COR or a reduced form thereof to a dimethylaminomethyl group; and
iii) if Y is not cyano, conversion of the group Y to a cyano group;

followed by isolation of citalopram base or a pharmaceutically acceptable acid addition salt thereof. The conversions mentioned under i), ii) and iii) above may be carried out in any order.

In a particular embodiment of the invention, the reduction of the double bond mentioned under i) above is carried out before the group —COR or a reduced form thereof is converted to a dimethylaminomethyl group as under ii) above.

Conversion of the group Y to a cyano group may be carried out at any suitable point during the reaction. In a particular embodiment, the compound of formula (III) used is a compound wherein Y is cyano.

According to a preferred embodiment of the invention, the compound of formula (III) is prepared by reaction of a compound of formula

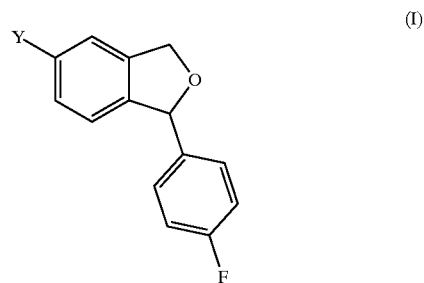

(I)

wherein Y is a cyano group or a group which may be converted to a cyano group, with a compound having the formula

(II)

wherein R is hydrogen, —O—R$^1$, —NH$_2$, —NHCH$_3$, —N(CH$_3$)$_2$ wherein R$^1$ is selected from h alkyl, alkenyl, alkynyl, and optionally alkyl substituted aryl or aralkyl; to form a compound of formula (III).

In another aspect, the present invention provides the novel intermediates of the general formula (III).

In yet another aspect, the present invention relates to an antidepressant pharmaceutical composition comprising citalopram manufactured by the process of the invention.

The group Y which may be converted to a cyano group may be selected from halogen, —O—SO$_2$—(CF$_2$)$_n$—CF$_3$, wherein n is 0–8, —CHO, —COOR', —CONR'R" or —NHR'" wherein R' and R" is selected from hydrogen, alkyl, alkenyl, alkynyl or optionally alkyl substituted aryl or aralkyl and R'" is hydrogen or alkylcarbonyl, or Y is a group of formula

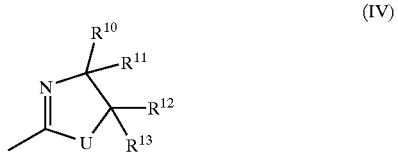

(IV)

wherein U is O or S;
R$^{12}$–R$^{13}$ are each independently selected from hydrogen and alkyl, or R$^{12}$ and R$^{13}$ together form a C$_{2-5}$ alkylene chain thereby forming a spiro ring; R$^{10}$ is selected from hydrogen and alkyl, R$^{11}$ is selected from hydrogen, alkyl, a carboxy group or a precursor group therefore, or R$^{10}$ and R$^{11}$ together form a C$_{2-5}$ alkylene chain thereby forming a spiro ring. Y may be any other group, which may be converted to a cyano group.

The alkylation step where the compound of formula (I) is reacted with a compound of formula (II) is suitably carried out by treatment of the compound of formula (I) with a base such as for example LDA (lithiumdiisopropylamine), LiHMDS (hexamethyldisilasan lithium), NaH, NaHMDS (hexamethyldisilasan sodium) or metalalkoxides such as NaOMe, KOMe, LiOMe, NaOtertBu, KOtertBu or LiOtertBu in an aprotic organic solvent such as THF (tetrahydrofuran), DMF (dimethylformamide), NMP (N-methylpyrrolidon), ethers such as diethylether or dioxalane, toluene, benzene, or alkanes and mixtures thereof. The anion formed is then reacted with a compound of formula (II) whereby a group of formula —CH=CH—COR is introduced into position 1 of the isobenzofuranyl ring system.

Compounds wherein the group —COR is —CON(CH$_3$)$_2$ may be converted to the corresponding compound wherein this group is a dimethylaminomethyl group by reduction, suitably in toluene using Red-Al as a reducing agent When —COR is —CONHCH$_3$ or —CONH$_2$, conversion to the dimethylaminomethyl group may be carried out by, in either order, reduction to form an amine and methylation or reductive amination form a dimethylaminomethyl group.

The reduction of the amide may be carried out in toluene using Red-Al as a reducing agent.

The methylation of the amine may be carried out with methylating agents such as MeI or Me$_2$SO$_4$, wherein Me is methyl. The methylation is carried out using conventional procedures for carrying out such reactions.

Alternatively, methylation to form a dimethylaminomethyl group is carried out by reductive amination. According to this procedure, the compound carrying a —NH$_2$ or a —NHCH$_3$ group is reacted with compounds such as formaldehyde, paraformaldehyde or trioxane in presence of a reducing agent such as NaBH$_4$ or NaBH$_3$CN. The reductive amination is carried out using conventional procedures for carrying out such reactions.

When R is —CHO, conversion to the dimethylaminomethyl group may be carried out by reductive amination with dimethylamine or a salt thereof. Suitably by reaction with dimethylamine in the presence of a reducing agent such as NaBH$_4$ or NaBH$_3$CN. Dimethylamine may be added to the reaction in the form of the dimethylammonium chloride salt or as a metal salt of dimethylamine.

When R is —COOR$^1$, the conversion to the dimethylaminomethyl group may be carried out by conversion to the corresponding amide followed by reduction, and optionally methylation or reductive amination to form a dimethylaminomethyl group.

The amide may be prepared by reaction of the ester with an amine, preferably NH(Me)$_2$ or a salt thereof.

When R is —COOR$^1$, the conversion of this group to the dimethylaminomethyl group may also be carried out by reduction to the corresponding alcohol followed by conversion of the alcohol group to a feasible leaving group and consecutively reaction
  a) with dimethylamine or a salt thereof,
  b) with methylamine followed by methylation or reductive amination to form a dimethylamino group, or
  c) with an azide followed by reduction to form the corresponding amino compound and thereafter methylation or reductive amination to form a dimethylamino group.

The alcohol may be formed from a compound wherein —COR is —COOR$^1$ by reduction of the ester using Red-Al as a reducing agent.

The alcohol group may be converted to a feasible leaving group such as halogen, or a sulphonate of formula —O—SO$_2$—R$^0$ wherein R$^0$ is alkyl, alkenyl, alkynyl or optionally alkyl substituted aryl or aralkyl, by reaction with reagents such as thionylchloride, mesylchloride, tosylchloride, etc.

The resulting compound carrying a suitable leaving group is then reacted with dimethylamine or a salt thereof, e.g. M$^+$, $^-$N(CH$_3$)$_2$ wherein M$^+$ is Li$^+$ or Na$^+$. The reaction is suitably carried out in an aprotic organic solvent such as THF (tetrahydrofuran), DMF (dimethylformamide), NMP (N-methyl pyrrolidon), ethers such as diethylether, or dioxalane, toluene, benzene or alkanes and mixtures thereof. The leaving group may also be replaced by dimethylamino by reaction with dimethylammonium chloride in presence of a base. Alternatively, the compound carrying a suitable leaving group, such as a sulphonate of formula —O—SO$_2$—R$^0$ wherein R$^0$ is as defined above, may be reacted with an azide, such as sodium azide, followed by reduction using Pd/C as a catalyst to form the free amino group and thereafter methylation or reductive amination to form a dimethylamino group.

The leaving group, may also be replaced by dimethylamino by reaction with methylamine followed by methylation or reductive amination to form a dimethylamine.

Methylation may be carried out with methylating agents such as MeI and Me$_2$SO$_4$, wherein Me is methyl. The methylation is carried out using conventional procedures for carrying out such reactions.

Alternatively, methylation is carried out by reductive amination as described above.

When Y is halogen or $CF_3$—$(CF_2)_n$—$SO_2$—O— wherein n is 0–8, the conversion to a cyano group may be carried out by reaction with a cyanide source, for example KCN, NaCN, CuCN, $Zn(CN)_2$ or $(R^{15})_4NCN$ where $(R^{15})_4$ indicates four groups which may be the same of different and are selected from hydrogen and straight chain or branched alkyl, in the presence of a palladium catalyst and a catalytic amount of $Cu^+$ or $Zn^{2+}$, or with $Zn(CN)_2$ in the presence a palladium catalyst. The conversion of a compound wherein Y is halogen, or $CF_3$—$(CF_2)_n$—$SO_2$—O— wherein n is 0–8, by reaction with a cyanide source in presence of a palladium catalyst, may be carried out as described in WO0013648.

When Y is Cl or Br the conversion to a cyano group may also be carried out by reaction with a cyanide source, for example KCN, NaCN, CuCN, $Zn(CN)_2$ or $(R^{15})_4NCN$ where $(R^{15})_4$ indicates four groups which may be the same of different and are selected from hydrogen and straight chain or branched alkyl, in the presence of a nickel catalyst. The conversion of a compound wherein Y is halogen or $CF_3$—$(CF_2)_n$—$SO_2$—O— wherein n is 0–8, by reaction with a cyanide source in presence of a nickel catalyst may be carried out as described in WO 0011926.

When Y is an oxazoline or a thiazoline of the formula (IV) the conversion to a cyano may be carried out as described in WO 0023431.

When Y is CHO, the conversion to a cyano group may be carried out by conversion of the formyl group to an oxime or similar group by reaction with a reagent of formula $R^{16}$—V—$NH_2$ wherein $R^{16}$ is hydrogen, alkyl, aryl or heteroaryl and V is O, N or S, followed by dehydration with a common dehydrating agent, for example thionylchloride, acetic anhydride/pyridine, pyridine/HCl or phosphor pentachloride. Preferred reagents $R^{16}$—V—$NH_2$ are hydroxylamine and compounds wherein $R^{16}$ is alkyl or aryl and V is N or O.

When Y is —COOH, the conversion to a cyano group may be carried out via the corresponding acid chloride, ester or amide.

The acid chloride is conveniently obtained by treatment of the acid with $POCl_3$, $PCl_5$ or $SOCl_2$ neat or in a suitable solvent, such as toluene or toluene comprising a catalytic amount of N,N-dimethylformamide. The ester is obtained by treatment of the acid with an alcohol, in the presence of an acid, preferably a mineral acid or a Lewis acid, such as HCl, $H_2SO_4$ $POCl_3$, $PCl_5$ or $SOCl_2$. Alternatively, the ester may be obtained from the acid chloride by reaction with an alcohol. The ester or the acid chloride may then converted to an amide of by amidation with ammonia or an alkylamine, preferably t-butyl amine.

The conversion to amide may also be obtained by reaction of the ester with ammonia or an alkylamine under pressure and heating.

The amide group is then converted to a cyano group by dehydration. The dehydrating agent may be any suitable dehydrating agent, and the optimal agent may easily be determined by a person skilled in the art. Examples of suitable dehydrating agents are $SOCl_2$, $POCl_3$ and $PCl_5$, preferably $SOCl_2$.

In a particularly preferred embodiment, the carboxylic acid is reacted is reacted with an alcohol, preferably ethanol, in the presence of $POCl_3$, in order to obtain the corresponding ester, which is then reacted with ammonia thereby giving the corresponding amide, which in turn is reacted with $SOCl_2$ in toluene comprising a catalytic amount of N,N-dimethyl-formamide.

Alternatively, a compound where Y is —COOH may be reacted with chlorosulfonyl isocyanate in order to form the nitrite, or treated with a dehydrating agent and a sulfonamide as described in WO 0044738.

When Y is —NHR''', where R''' is hydrogen, the conversion into cyano is preferably performed by diazotation and followed by reaction with $CN^-$. Most preferably, $NaNO_2$ and CuCN and/or NaCN is used. When R''' is alkylcarbonyl, the compound is initially subjected to hydrolysis thereby obtaining the corresponding compound wherein R''' is H which is then converted as described above. The hydrolysis may be performed either in acidic or basic environment.

Starting materials of formula (I) wherein Y is halogen may be prepared as described in GB 1526331; compounds of formula (I) wherein Y is —O—$SO_2$—$(CF_2)_n$—$CF_3$ may be prepared analogously to the compounds described in WO 99/00640; compounds of formula (I) wherein Y is an oxazoline or a thiazoline group may be prepared analogous to the compounds described in WO 00/23431; compounds wherein Y is formaldehyde may be prepared analogously to the compounds described in WO 99/30548; compounds wherein Y is —COOH, and esters and amides thereof, may be prepared analogously to the compounds described in WO 98/19511; and compounds of formula I wherein is —NHR''' may be prepared analogously to the compounds described in WO 98/19512.

The reaction conditions, solvents, etc. used for the reactions described above are conventional conditions for such reactions and may easily be determined by a person skilled in the art.

The starting material, of formula (I) wherein Y is a cyano group may be prepared as described in U.S. Pat. No. 4,136,193 or as described in WO 98/19511.

The compounds of formula (II) are commercially available or may be prepared form commercially available starting materials using conventional techniques.

Citalopram is on the market as an antidepressant drug in the form of the racemate. However, in the near future, the active S-enantiomer of citalopram is also going to be introduced to the market.

S-citalopram may be prepared by separation of the optically active isomers by chromatography.

Throughout the specification and claims, the term alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl.

Similarly, alkenyl and alkynyl, respectively, designate such groups having from two to six carbon atoms, including one double bond and triple bond respectively, such as ethenyl, propenyl, butenyl, ethynyl, propynyl, and butynyl.

The term aryl refers to a mono- or bicyclic carbocyclic aromatic group, such as phenyl and naphthyl, in particular phenyl.

The term aralkyl refers to aryl-alkyl, wherein aryl and alkyl is as defined above.

Optionally alkyl substituted aryl and aralkyl refers to aryl and aralkyl groups, which may optionally be substituted with one or more alkyl groups.

Halogen means chloro, bromo or iodo.

Citalopram may be used as the free base, in particular in crystalline form, or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of citalopram may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual, sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive, colourings, aroma, preservatives etc. may be used provided that they are compatible with the active ingredients.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

The invention is further illustrated by the following examples.

EXAMPLE 1

A solution of 1-(4-fluorophenyl)-1,3-dihydroisobenzofuran-5-carbonitrile (4.8 g, 0.02 mol) in THF (50 mL) was added dropwise to a solution of LDA (Butyl lithium 1.6 M (15 mL), disopropylamine 2.6 g) at −30° C. under an atmosphere of nitrogen. After stirring at −30° C. for 10 minutes a solution of a compound of formula (II) (0.02 mol) in THF (25 mL) was added dropwise and allowed to warm to room temperature and stirred for a further 60 minutes. The reaction was then quenched with ice, extracted with toluene (3×50 mL), washed with water (50 mL) and concentrated under reduced pressure. The residue was purified by chromatography on silica gel using mixtures of n-heptane/EtOAc as the eluent.

What is claimed is:

1. A method for the preparation of citalopram comprising subjecting, in either order, a compound of formula

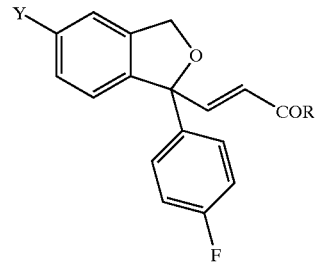

(III)

wherein Y is a cyano group or a group which may be converted to a cyano group, R is hydrogen, —O—R$^1$, NH$_2$, NHCH$_3$ or —N(CH$_3$)$_2$ wherein R$^1$ is selected from hydrogen, alkyl, alkenyl, alkynyl and optionally alkyl substituted aryl or aralkyl; to
  i) reduction of the double bond in the side chain of formula —CH=CH—COR;
  ii) conversion of the group —COR or a reduced form thereof to a dimethylaminomethyl group; and
  iii) if Y is not cyano, conversion of the group Y to a cyano group;
  followed by isolating citalopram base or a pharmaceutically acceptable acid addition salt thereof.

2. The method of claim 1 wherein the compound of formula (III) is prepared by reacting a compound of formula

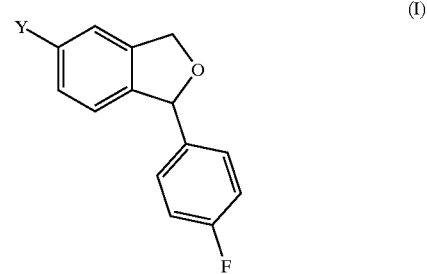

(I)

wherein Y is a cyano group or a group which may be converted to a cyano group, with a compound having the formula

(II)

wherein R is hydrogen, —O—R$^1$, —NH$_2$, —NHCH$_3$ or —N(CH$_3$)$_2$ wherein R$^1$ is selected from alkyl, alkenyl, alkynyl, and optionally alkyl substituted aryl or aralkyl; to form a compound of formula (III).

3. The method of claim 1, wherein —COR is —CON(CH$_3$)$_2$ and the conversion of the —CON(CH$_3$)$_2$ group to dimethylaminomethyl is carried out by reduction.

4. The method according to claim 1, wherein —COR is —CONHCH$_3$ or —CONH$_2$ and the conversion of the —CONHCH$_3$ or —CONH$_2$ groups is carried out by, in either order, reduction and methylation or reductive amination to form a dimethylaminomethyl group.

5. The method of claim 1 wherein COR is —CHO and the conversion to dimethylaminomethyl is carried out by reductive amination with dimethylamine or a salt thereof.

6. The method of claim 1 wherein COR is —COOR$^1$ and the conversion to the dimethylaminomethyl group is carried out by conversion to the corresponding amide followed by reduction and optionally methylation or reductive amination to form a dimethylaminomethyl group.

7. The method of claim 1 wherein COR is —COOR$^1$ and the conversion of the —COOR$^1$ group to dimethylaminomethyl is carried out by reduction to the corresponding alcohol, followed by conversion of the alcohol group to a feasible leaving group and consecutively reaction
   a) with dimethylamine or a salt thereof,
   b) with methylamine followed by methylation or reductive amination to form a dimethylamino group, or
   c) with an azide followed by reduction to form the corresponding amino compound and thereafter methylation or reductive amination to form a dimethylamino group.

8. A compound having the formula

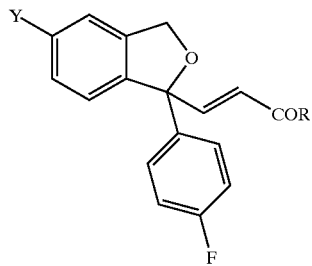

(III)

wherein Y is a cyano group or a group which can be converted to a cyano group, R is hydrogen, —O—R$^1$, NH$_2$, NHCH$_3$ or —N(CH$_3$)$_2$ wherein R$^1$ is selected from hydrogen, alkyl, alkenyl, alkynyl and optionally alkyl substituted aryl or aralkyl, or an acid addition salt thereof.

9. The method of claim 1, wherein Y is a cyano group or a group which may be converted to a cyano group which is selected from the group consisting of halogen, —O—SO$_2$—(CF$_2$)$_n$—CF$_3$, wherein n is 0-8, —CHO, —COOR', —CONR'RΔ or NHR''' wherein R' and R'' are selected from hydrogen, alkyl, alkenyl, alkynyl or optionally alykyl substituted aryl or aralkyl and R''' is hydrogen or alkylcarbonyl, or Y is a group of formula

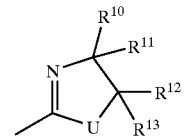

wherein U is O or S

R$^{12}$ and R$^{13}$ are each independently selected from hydrogen and alkyl, or R$^{12}$ and R$^{13}$ together from a C$_{2-5}$ alkylene chain thereby froming a spiro ring; R$^{10}$ is selected from hydrogen and alkyl, R$^{11}$ together form a C$_{2-5}$ alkylene chain thereby forming a spiro ring.

10. The compound of claim 8, wherein Y is a cyano group or a group which may be converted to a cyano group which is selected from the group consisting of halogen, —O—SO$_2$—(CF$_2$)$_n$-CF$_3$, wherein n is 0-8, —CHO, —COOR', —CONR'R'' or NHR''' wherein R' and R'' are selected from hydrogen, alkyl, alkenyl, alkynyl or optionally alkyl substituted aryl or aralkyl and R''' is hydrogen or alkylcarbonyl, or Y is a group of formula

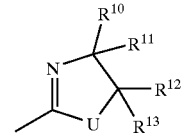

wherein U is O or S

R$^{12}$ and R$^{13}$ are each independently selected from hydrogen and alkyl, or R$^{12}$ and R$^{13}$ together form a C$_{2-5}$ alkylene chain thereby forming a spiro ring; R$^{10}$ is selected from hydrogen and alkyl, R$^{11}$ is selected from hydrogen, alkyl, a carboxy group or a precursor group therefore, or R$^{10}$ and R$^{11}$ together form a C$_{2-5}$ alkylene chain thereby forming a spiro ring.

* * * * *